United States Patent
Linares et al.

(10) Patent No.: US 9,095,345 B2
(45) Date of Patent: Aug. 4, 2015

(54) TISSUE AND BONE GRAFT REMOVAL DEVICE

(71) Applicant: Linares Medical Devices, LLC, Auburn, MI (US)

(72) Inventors: Miguel A. Linares, Bloomfield Hills, MI (US); Miguel A. Linares, Jr., Bloomfield Hills, MI (US); Ryan T. Greene, Bloomfield Hills, MI (US)

(73) Assignee: Linares Medical Devices, LLC, Auburn Hills, MI (US)

( * ) Notice: Subject to any disclaimer, the term of this patent is extended or adjusted under 35 U.S.C. 154(b) by 53 days.

(21) Appl. No.: 13/787,435

(22) Filed: Mar. 6, 2013

(65) Prior Publication Data

US 2013/0237843 A1    Sep. 12, 2013

Related U.S. Application Data (60) Provisional application No. 61/607,219, filed on Mar. 6, 2012.

(51) Int. Cl.
*A61B 17/14* (2006.01)
*A61B 17/16* (2006.01)
(Continued)

(52) U.S. Cl.
CPC ............ *A61B 17/141* (2013.01); *A61B 17/1606* (2013.01); *A61B 17/1659* (2013.01); *A61B 19/5225* (2013.01); *A61B 2017/00561* (2013.01); *A61B 2017/00734* (2013.01); *A61B 2017/143* (2013.01); *A61B 2019/521* (2013.01)

(58) Field of Classification Search
CPC ............ A61B 17/141; A61B 17/1635; A61B 17/1604; A61B 2017/143
USPC .............. 606/79, 82, 83; 600/565, 568
See application file for complete search history.

(56) References Cited

U.S. PATENT DOCUMENTS 4,722,338 A    2/1988    Wright et al.
4,733,663 A    3/1988    Farley
(Continued)

OTHER PUBLICATIONS

Angled Kerrison Rongeur, www.neurosurvival.ca/computerassistedlearning/surgical_technique_equipment/equipment_Kerrison_Rongeur.htm, dated Feb. 6, 2012, 1 page.

*Primary Examiner* — Sean Dougherty
*Assistant Examiner* — Megan Leedy
(74) *Attorney, Agent, or Firm* — Gifford, Krass, Sprinkle, Anderson & Citkowski, P.C.; Douglas J. McEvoy (57) ABSTRACT

The present invention discloses a rongeur type bone and cartilage removal device incorporating a pistol shaped body exhibiting a forward extending barrel terminating in a powered saw drive including a plurality of blades. A passageway extends through an interior of the barrel and communicates the forward chain drive with a rearward positioned debris collection chamber. A power supply is incorporated into the body and, upon actuating a trigger, closes a circuit with the saw drive and a separate vacuum inducing drive in order to successively excise increments of bone for evacuation through the passageway and into the collection chamber. Another variant of the rongeur type bone removal device includes first and second pivotally secured handles, the first handle terminating at a forward end in a first jaw exhibiting a plurality of extending teeth, with second handle terminating in a second jaw opposing the first jaw and exhibiting a continuous blade edge against which the teeth seats during pivotal motion of the jaws.

7 Claims, 8 Drawing Sheets

(51) Int. Cl.
　　　*A61B 19/00*　　　(2006.01)
　　　*A61B 17/00*　　　(2006.01)

(56) References Cited

U.S. PATENT DOCUMENTS

| | | |
|---|---|---|
| 4,777,948 A | 10/1988 | Wright |
| 5,026,375 A | 6/1991 | Linovitz et al. |
| 5,061,269 A | 10/1991 | Muller |
| 5,273,519 A | 12/1993 | Koros et al. |
| 5,385,570 A | 1/1995 | Chin et al. |
| 5,451,227 A | 9/1995 | Michaelson |
| 5,582,618 A | 12/1996 | Chin et al. |
| 5,653,713 A | 8/1997 | Michelson |
| 5,782,849 A | 7/1998 | Miller |
| 6,142,997 A | 11/2000 | Michelson |
| 6,200,320 B1 | 3/2001 | Michelson |
| 6,221,007 B1 * | 4/2001 | Green .......... 600/160 |
| 6,575,977 B1 | 6/2003 | Michelson |
| 6,695,849 B2 | 2/2004 | Michelson |
| 7,011,683 B2 | 3/2006 | Michelson |
| 7,297,147 B2 | 11/2007 | Michelson |
| 7,637,872 B1 * | 12/2009 | Fox .......... 600/562 |
| 7,922,723 B2 | 4/2011 | Michelson |
| 8,241,290 B2 | 8/2012 | Michelson |
| 2007/0213735 A1 * | 9/2007 | Saadat et al. .......... 606/79 |
| 2010/0179557 A1 | 7/2010 | Husted |

\* cited by examiner

TISSUE AND BONE GRAFT REMOVAL
DEVICE

CROSS-REFERENCE TO RELATED
APPLICATIONS

This application claims the benefit of U.S. Provisional Application 61/607,219 filed on Mar. 6, 2012, the contents of which are incorporated herein in its entirety.

FIELD OF THE INVENTION

The present invention is directed to a bone and tissue removal device, such as is known as a rongeur type instrument (French for rodent or gnawer) which is used for opening a window in a bone for any number of purposes not limited to neurosurgery (skull) or orthopedic (musculoskeletal) surgery, as well as oral maxillofacial, hand or other surgical procedures. The removal device according to the present invention improves upon prior art "rongeur" type instruments and provides a first pistol shaped variant incorporating a powered and continuous chain scoop saw drive with enclosed collection chamber for retaining incised bone and tissue debris. A second manual pliers type variant is also disclosed with alligator type gnawing teeth incorporated into a first jaw which aligns with an opposing and depth defining collection chamber exhibiting an upper razor edge associated with a second jaw, an ejection mechanism including an elongated and pivotally actuated scoop which is operable to eject previously collected debris from within the collection chamber of the second jaw.

BACKGROUND OF THE INVENTION

Rongeur surgical cutting instruments are known in the art for removing sections of bone or cartilage. Notable examples of these include the surgical rongeurs depicted in each of U.S. Pat. No. 5,653,73 and U.S. Pat. No. 6,142,997 and which disclose two shaft members capable of reciprocating motion relative to each other wherein one shaft member terminates in a foot plate and the other shaft member includes a combined cutting element and disposable storage chamber. The rongeur may be manually activated or solenoid powered by a battery.

A further example of an adjustable powered rongeur is depicted in US 2010/0179557 to Husted and which teaches an adaptable deburring bit and independent nerve sensors that facilitate positioning of the instrument to a proximate surgery site. The medical instrument has a hand piece on a proximal end of a shaft and a hollow tip portion on a distal end of the shaft. The hand piece includes a handgrip and a squeezable trigger portion, whereby the trigger portion is independently compressible of the handgrip. The trigger portion controls a rotatable surgical tool bit which is housed in the tip portion and powered by a connecting drive system. A safety apparatus is provided on the grip portion, capable of locking the instrument and a monitoring system disposed on the tip portion, in order to identify proximity of nerve endings.

SUMMARY OF THE INVENTION

The present invention discloses a rongeur type bone and cartilage removal device incorporating a pistol shaped body exhibiting a forward extending barrel terminating in a powered saw drive including a plurality of blades. A passageway extends through an interior of the barrel and communicates the forward chain drive with a rearward positioned debris collection chamber. A power supply is incorporated into the body and, upon actuating a trigger, closes a circuit with the saw drive and a separate vacuum inducing drive in order to successively excise increments of bone for evacuation through the passageway and into the collection chamber.

A video monitor is mounted to a rear location of the body and is communicable with a processor/controller for imaging a target area. The power supply can further be incorporated into a handle portion of the body.

The chain drive may further incorporate at least one of an elongated conveyor drive or a rotary drive, with the blades each further exhibiting an arcuate scoop shape with an outer extending blade edge. Alternatively, the forward chain drive may include an attachment which is removably engageable to the forward barrel end and substitutable with other configured chain drives.

Another variant of the rongeur type bone removal device includes first and second pivotally secured handles, the first handle terminating at a forward end in a first jaw exhibiting a plurality of extending teeth, with second handle terminating in a second jaw opposing the first jaw and exhibiting a continuous blade edge against which the teeth seats during pivotal motion of the jaws in order to successively excise increments of bone for evacuation through the passageway and into the collection chamber. The first and second jaws each exhibit an elongated and depth defining shape, with the first jaw being an upper and downwardly open jaw and the second jaw being a lower and upwardly open jaw.

A pivotally actuated scoop can be associated with the second lower jaw for removing previously stored debris. A finger projection extends from a pivotal washer shaped portion in a direction opposite a forward projecting direction of the scoop, a tab extending from the finger and seating in a first position within an underside of the second handle in engagement with a forward end location of an embedded stem.

Yet additional features include a coil spring seating within the second handle and biasing against the finger. A push button being incorporated into a remote location of the second handle and, upon being depressed, permitting a second coil spring embedded in a rear location of the second handle to cause a linear retraction of the embedded stem resulting in release of the tab and subsequent upward pivoting of the scoop.

BRIEF DESCRIPTION OF THE DRAWINGS

Reference will now be made to the attached drawings, when read in combination with the following detailed description, wherein like reference numerals refer to like parts throughout the several views, and in which:

FIG. 10 is a similar view to that shown in FIG. 9 and illustrating the selected trigger mechanism incorporating handle and integrally extending jaw in lengthwise cutaway in order to better depict inner working mechanism operable upon depressing the handle located button for pivotally actuating the coaxially supported and elongated scoop from within the collection chamber interior of the jaw for ejecting previously collected debris from.

DETAILED DESCRIPTION OF THE PREFERRED EMBODIMENTS

Figure 1:
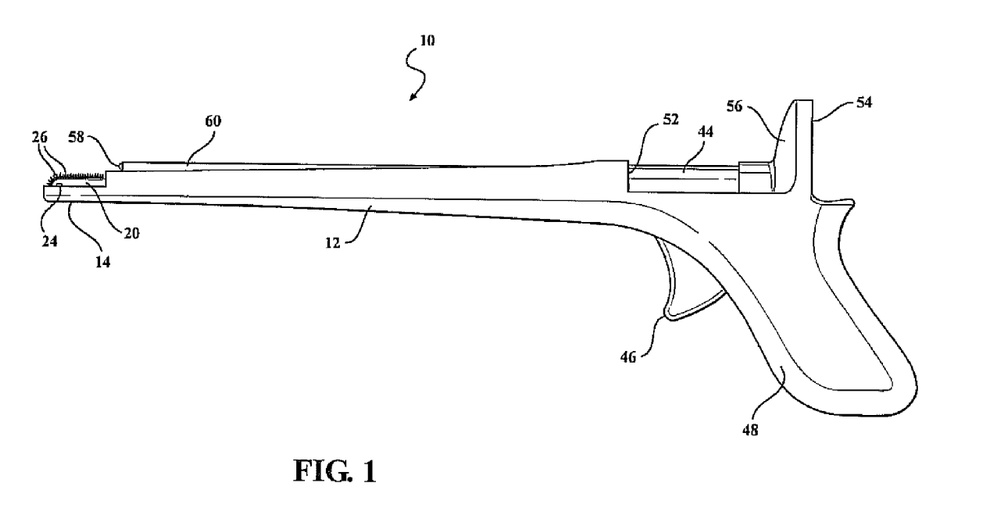
FIG. 1 is an illustration of a pistol styled powered tissue and bone graft removal device according to a first embodiment including continuous chain scoop saw drive with enclosed collection chamber for retaining incised bone and tissue debris.

Referring now to FIG. 1, an illustration is generally shown at 10 of a pistol styled powered tissue and bone graft removal device according to a first non-limiting embodiment. As is also depicted in succeeding FIGS. 2-6, the device includes a generally elongated barrel 12 terminating at a forward end in a continuous chain scoop saw drive, this being configured as either an integrally formed or separable forward attachment 14.

Figure 3:
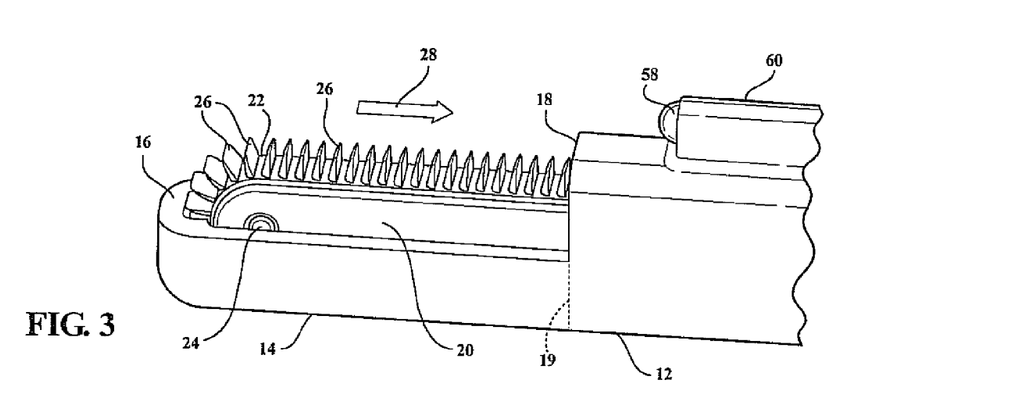
FIG. 3 is an enlarged forward end perspective better illustrating the configuration of the chain scoop drive in relation to the video imaging (and optionally light illuminating) lens for providing effective, targeted and efficient bone and tissue removal.

As better shown in FIG. 3, the forward scoop saw drive 14 exhibits an open region defined by an exposed upper surface 16 which extends to a forward edge surface 18 of the main barrel 12, such as in order to mount the forward attachment 14. Dashed line 19 in FIGS. 3-4 can represent a separating location established between a removable variant of the forward drive attachment 14 and the forward edge surface 18 of the barrel 12.

Figure 6:
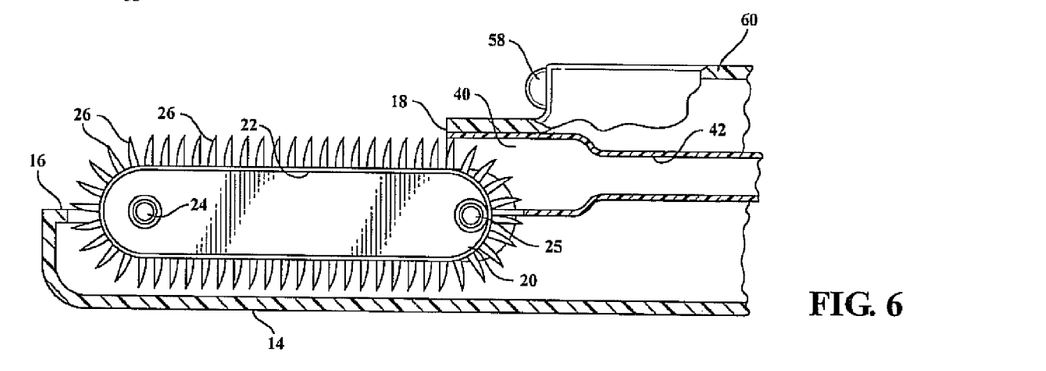
FIG. 6 is a side line art depiction of the chain scoop variant depicted in FIG. 3 and depicting both the interchangeable nature of the end attachment incorporating the chain scoop, as well as the suction inducing conduit built into the barrel for inducing removal and collection of debris within the rear located collection chamber.
Figure 7:
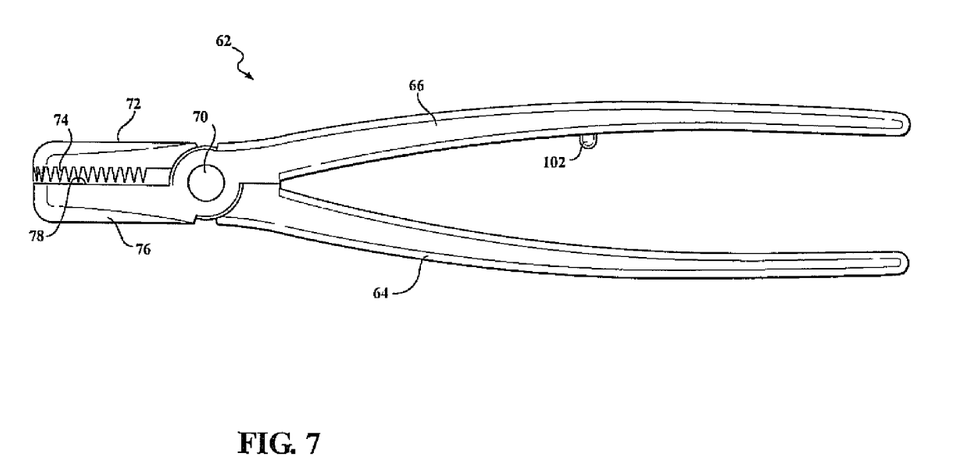
FIG. 7 is a side view of a manual pliers type variant is also disclosed with alligator type gnawing teeth incorporated into a first jaw which aligns with an opposing and depth defining collection chamber exhibiting an upper razor edge associated with a second jaw.

The scoop drive includes an elongated conveyor support 20 which supports a belt 22 in continuous loop fashion upon the support 20, this as best depicted by forward located drive pin 24 (FIGS. 2-3) as well as identical rear drive pin 25 in the line art view of FIG. 6. The conveyor support 20, along with the body of the pistol device 12, can be construed of a durable plastic, such as exhibiting sanitized or antimicrobial properties. The construction of the belt 22 is further such that it exhibits a durable and flexible consistency (such as including a varying durometer graded plastic or other synthetic material) and which is either keyed or frictionally driven along the outer contours of the conveyor supported elongated body 20.

A plurality of individual scoop shaped blades 26 are depicted, such as each exhibiting a generally paddle type body with an outer incising edge for scraping or abrading the surface desired to be excised or eroded. As further shown, the blades 26 are depicted in an outwardly extending and closely spaced apart fashion and at linearly spaced intervals along the closed belt 22 and so that, upon activating a power source for driving the belt (such as located in an associated handle or stock portion of the pistol), the scoop shaped blades 26 are caused to rapidly translate in successive abrading fashion.

As a result, and upon being positioned in contact with a bone, cartilage, tissue or other growth such as existing within a body cavity of a patient, the rapid linear movement of the scoops mounted to the belt conveyor supported results in the configured blades 26 successively abrading or sectioning along the target zone, the result of which is that the excess bone or cartilage material is to be rapidly and successively abraded or removed. Although not shown, it is envisioned that any type of bevel, screw or other drive or gearing arrangement, as well as other variants not limited to such as electromagnetic type drive outputs, can be incorporated into the pistol type rongeur device and which is activated in order to drive the conveyor supported belt 22 and, thereby, the individual scoop shaped projections 26 in the direction depicted by arrow 28 in FIG. 3 in order to quickly abrade or erode away the undesirable material.

Figure 5:
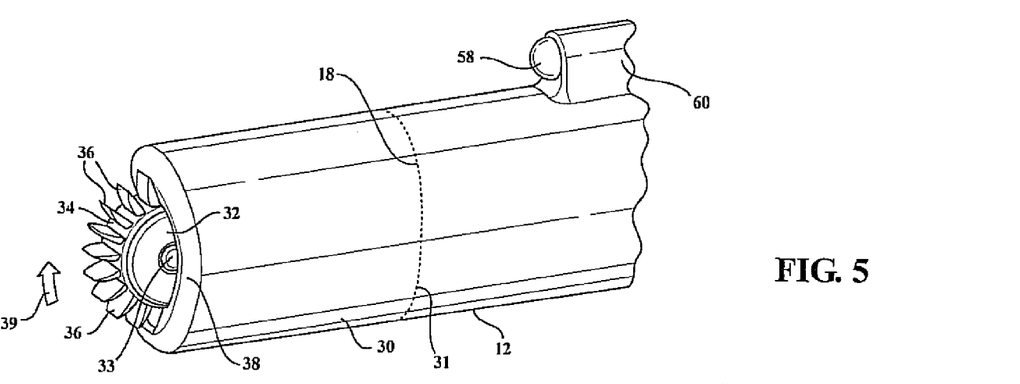
FIG. 5 is an illustration similar to FIG. 3 of an alternately configured "paddle wheel" style scoop for providing more target incising and removal of bone and/or tissue debris, such further contemplating a forward end attachment operable with a standard gearing construction built into the body of the trigger style pistol shaped body, such capable of being interchangeably engaged with the pistol style device along with any number of separate end attachments exhibiting different powered collection scoops and/or sectioning configurations.

The construction of the scoop drive can be further reconfigured to that shown by three dimensional forward portion 30 (which again can be either integrally formed to the main barrel 12 or alternately separably attachable, such as along a separation line 31) and as a substitute attachment to the chain scoop of FIG. 3. FIG. 5 depicts an alternately configured "paddle wheel" style scoop in which a reconfigured support element 32 is provided in rotatably supported fashion, at 33 to the forward exposed location of the barrel, and upon which is exhibited an outer surface 34 mounting a rotary extending and driven pattern of scoop type blades 36 located at a forward mounted edge of the attachment housing 30 and which is exposed by an inwardly arcuately recessed or tapered forward edge 38 of the housing 30.

The direction of the rotating scoop type blades 36 (see arrow 39 in FIG. 5) results in excised or abradingly removed debris being withdrawn into the interior of the attachment 30 and, by virtue of a vacuum collection inlet 40 (see FIG. 6) is positioned at an interior entrance location of the main barrel 12. This causes the debris and other particles to be conveyed rearwardly along an interconnecting vacuum passageway 42 for collection within the rear collection chamber. Although not shown, it is understood that any suitable design or variant of a vacuum inducing element, such as inner positioned and rotating element, can be incorporated into the barrel 12 at a location between its forward edge and a rear delivery location associated with the attachable debris reservoir, and which also draws power from the power supply (such as located within the handle or stock).

As previously described, any number of different attachments, such as representatively shown at 14 and 30 in FIGS. 3 and 5, respectively, can be provided for assisting in scraping, gouging or other suitable abrading removal of bone, tissue or other types of growth. As previously indicated, additional variants can include the forward scoop shaped blades such as depicted in either of the attachments 14 and 30 being incorporated into a one-piece integrally formed pistol body and so that a kit of pistol (or other handheld or carryable) devices are provided, each with a variously configured forward end incising/excavating subassembly.

Referring again to FIGS. 1-2, additional features associated with the powered rongeur type removal device 10 include an enclosed collection chamber, such as is depicted by a cylindrical shaped enclosure 44 exhibiting a transparent wall and which seats within a mating recess profile defined in a rear location of the main pistol body proximate to an activating trigger 46 and a rear handle or stock 48 (such as further retaining any type of alkaline, Lithium ion or other disposable/rechargeable battery or like power supply which may be accessible through a battery door such as located in a bottom of the handle, as well as a charging port likewise accessible through a stock or handle proximate location in order to recharge certain types of battery power supplies). An associated wiring protocol according to any known construction ensures that, upon the trigger 46 being depressed, a circuit is closed between the power supply and the gearing or drive components for activating the blade scoop assembly in the manner previously described.

Figure 2:
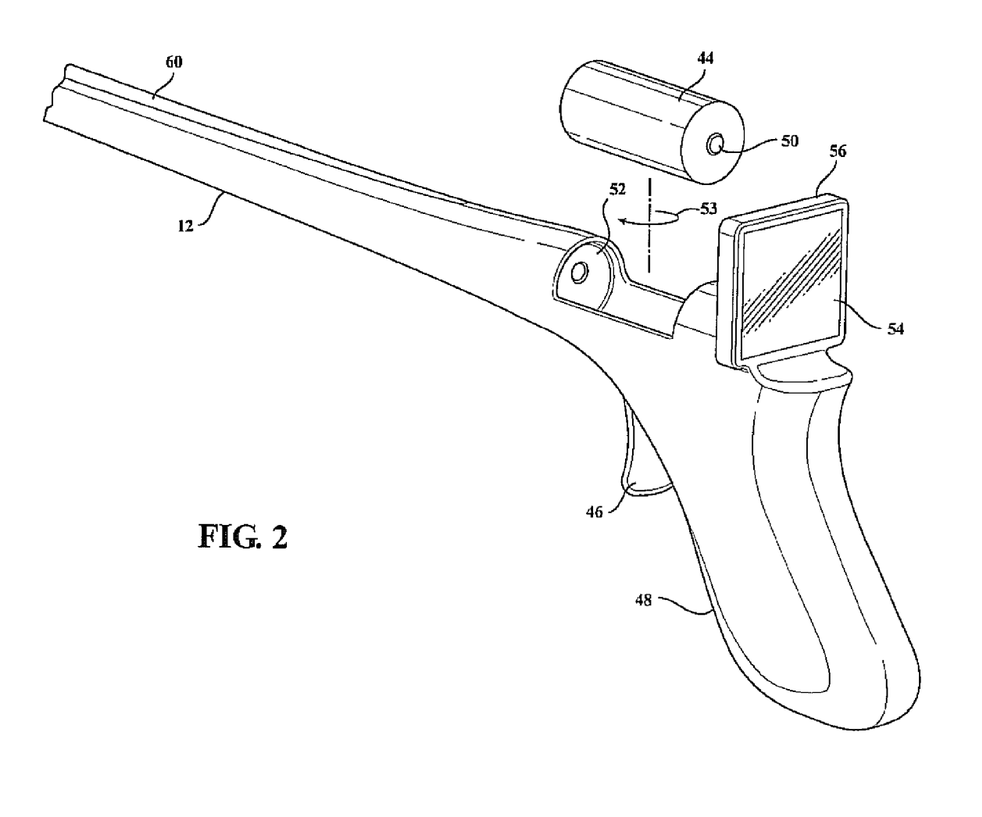
FIG. 2 is a rotated perspective of the powered removal device of claim 1 and better illustrating the features of the sealed debris collection chamber, such as designed as a removable cylindrical component capable of quick replacement with an identical component when filled so as to permit continuous use, as well as a mini video screen built into a handle proximate rear location, this interfacing with a processor for providing enhanced or magnified three dimensional imaging of a target area.

As best shown in FIG. 2, the collection chamber 44 includes a forward nipple or like apertured location 50 (see also replacement collection chamber 44 shown in FIG. 2) which aligns with a similar aperture formed in a forward disk or annular shaped wall, see at 52, defining a corresponding forward end of the receiving location associated with a rear end location of the barrel 12 (it further noted that the cylindrical collection chamber 44 shown in FIG. 2 being rotated in the direction of arrow 53 in order to align the nipple location 50 with the aperture 52 in the rear interior of the barrel 12). This design permits a first collection chamber 44 to be quickly detached and removed or otherwise ejected from the exposed top of the pistol body, such as upon visual notification of it having been filled with bone or other aggregating debris which passes from the vacuum passageway 42 into the transparent walled and three dimensional cylindrical receptacle. It is further envisioned that the nipple location 50 and seating aperture 52 can incorporate additional structure (not shown) which, during removal and replacement of a first cylindrical chamber defining component 44 with an identical second component, prevents spillage of debris within the interior vacuum passageway 42 of the barrel 12, such a port being reestablished upon attachment/reattachment with a succeeding collection component 44.

Additional features include a video display 54 supported within an integral rear portion 56 of the pistol above the hand grip 48, the video display interfacing with an associated processor or controller (not shown but understood to be incorporated into a suitable location of the pistol body such as in proximity to the hand grip and contained power source). A lens 58 is positioned at a forward facing end of the barrel 12 (see as best shown in FIGS. 3-6) and communicates, via an upper edge extending passageway 60 integrated into the main barrel along with any suitable fiber optic or other type wiring, extending to the embedded processor/controller and the video screen 54 to assist with imaging the interior of the cavity within which the forward attachments 14 or 30 are positioned and to better calibrate and control the parameters surrounding removal of the excess bone, tissue or other typically hardened growths.

Additional features can include an additional light illuminating source, such as an LED type element, which is integrated into the pistol body and assists in the imaging aspects of the design. The associated controller can also be designed to provide varying resolutions and/or (three dimensional) magnification to ensure that as detailed an image of the target area is provided as possible in order to ensure proper abrading or excising of the location. Depending upon the target area being illuminated, it is further envisioned that the controller can further provide different imaging patterns (thermal, nuclear, other luminescent or the like) depending upon the removal application being employed for providing effective, targeted and efficient bone and tissue removal. Additional controller features can include, without limitation, the ability to determine mass, type, and density of the material being removed and retained within the collection chamber 44.

Figure 4:
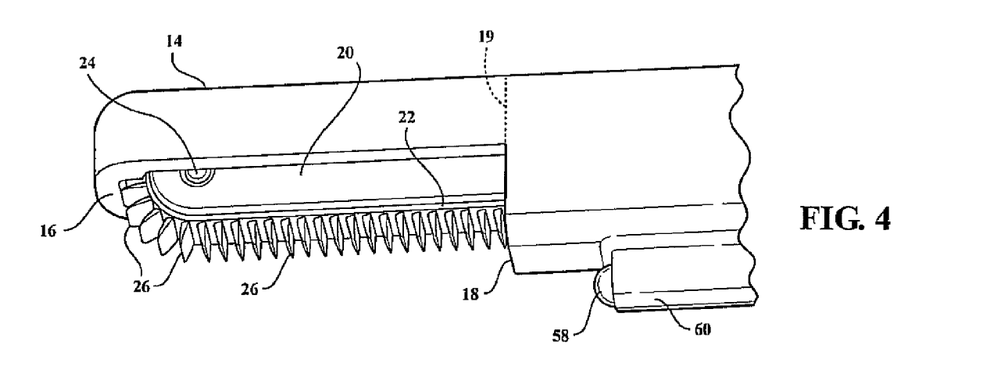
FIG. 4 is an inverted/rotated illustrating of the forward and chain scoop drive defining end and which illustrates from another perspective the manner in which the tool can be repositioned in order to section bone and tissue, such as without loss of efficiency and as a result of the vacuum inducing aspect incorporated into the device for suctioning the incised or section bone/tissue debris.

FIG. 4 depicts an inverted/rotated illustrating of the forward and chain scoop drive defining end attachment 14, and which illustrates from another perspective the manner in which the tool can be repositioned in order to section bone and tissue. The purpose of this view is to highlight that the barrel end of the tool can be positioned at any angle during use, without loss of efficiency, such as which is maintained by the vacuum inducing aspects previously described for suctioning the incised or section bone/tissue debris.

Figure 8:
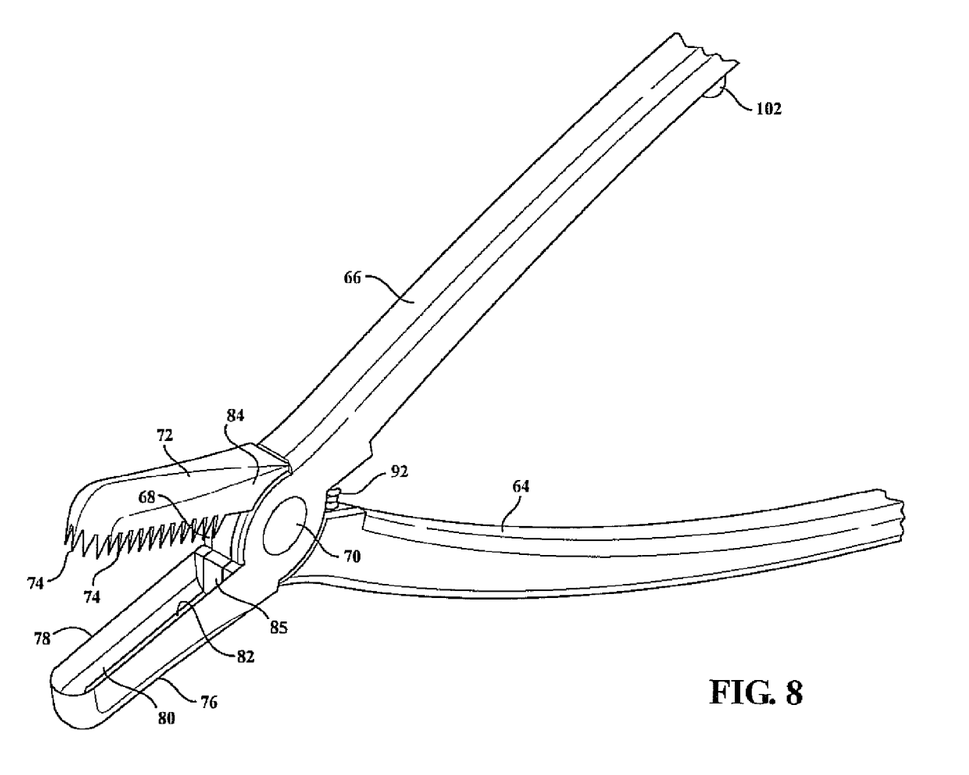
FIG. 8 is a rotated perspective of the manual pliers type variant of FIG. 7 and which better depicts the pivotally opposing and incising nature of the upper alligator teeth and opposing elongated collection chamber with upper facing and continuous razor edge.
Figure 9:
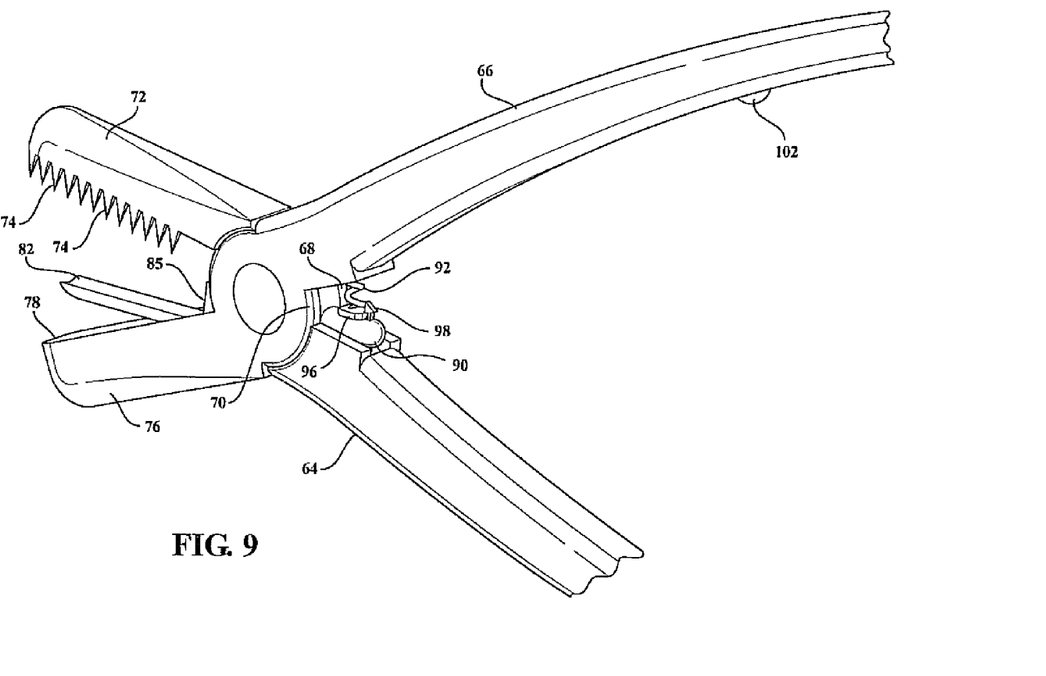
FIG. 9 is a rotated rear facing view of the pliers type variant of FIG. 7 and better illustrating an external depiction of a trigger ejection mechanism for removing debris from the collection chamber via a pivotally actuated scoop.
Figure 10:
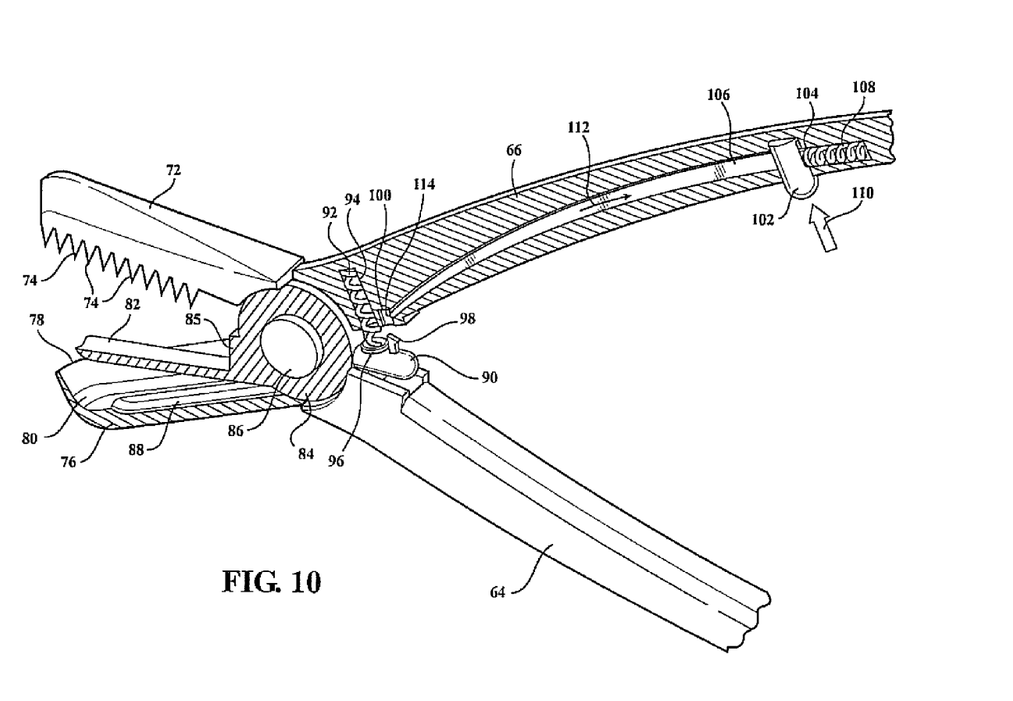

Referring to FIGS. 7-10, a series of side, perspective and cutaway views are generally shown at 62 of a further manual pliers type variant. The pliers type rongeur device operates under a similar principle as the powered variant (with the exception that it incises or removes a small volume of bone or the like with each iteration or bite) and includes a first handle 64 and a second handle 66. Each of the handles 64 and 66 are contoured along their rear extending grasping portions and each includes a circular overlapping and pivotally joined portions 68 and 70, respectively (see as best shown in FIG. 10 perspective).

The first handle 64 terminates forwardly of its pivotally overlapping portion 68 in an integrally formed upper jaw 72 exhibiting an elongated depth defining and downwardly open profile integrating a continuous plurality of alligator type gnawing teeth 74.

The second handle 66 likewise terminates forwardly of its pivotally overlapping portion 70 in a like integrally formed and upwardly open facing and depth defining lower jaw 76 which exhibits a substantially identically configured contour as the upper jaw 72. The lower jaw 76 exhibits an upper continuous blade edge 78 and which matches the profile of the downwardly facing teeth 74 so that that, upon positioning the jaws 72 and 76 on opposite sides of a section of bone to be removed, inward compression on the handles results in the jaws pivoting together and the teeth 74 abut the opposite continuous razor or blade edge 78 concurrent with a volume of bone or like debris being excised or "bitten off" and deposited within an interior chamber 80 (see FIGS. 8 and 10) defined in the lower jaw 76.

With reference to FIGS. 8-10, additionally illustrated is a trigger ejection mechanism for assisting in easy ejection of previously deposited bone and like debris from within the lower jaw collection chamber 80. The ejection mechanism includes an elongated scoop 82 extending from a pivotally supported washer shaped portion 84 (see as best shown in FIG. 10 and in which the scoop 82 is connected to the washer 84 via a stepped location 85) which is mounted upon coaxial pin or hub 86 so that the elongated scoop 82 (exhibiting an arcuate profile in cross section) pivots from a first recessed seating location (FIG. 8) in which the scoop seats within a recessed matching base inner profile 88 (FIG. 10) to a second upwardly pivoted location (FIGS. 9 and 10) in which the scoop 82 upwardly ejects the debris from within the chamber.

As again best shown in FIG. 10, additional features incorporated into the trigger ejection mechanism include an integral rearwardly projecting finger 90 extending from the coaxially supported washer shaped 84. A coil spring 92 seats within an inner elongated and recessed profile, at 94, defined in depth extending fashion from an underside accessible location of the second handle 66 proximate the overlapping portions 68/70 of the jaws 64/66, with a base mounting location 96 of the spring 92 engaging the finger projection 90 offset from its pivot fulcrum provided by the coaxial mounting hub 86.

A tab 98 extends upwardly from a rearward proximate end of the finger 90 rearwardly of the coil spring 92 and seats within a mating recess profile 100 defined in a rearwardly spaced and downwardly communicating location of the upper handle 66 which is proximate to the inner seating location of the spring 92 as again shown in FIG. 10. A push button 102 is spring biased at a mounted at a rearward location of the upper handle 66 and exhibits an inner slot 104 through which is received a rearward extending end of an elongated stem 106 embedded within an elongated recess defined in the handle 66, with a second coil spring 108 extending linearly on a rear side of the button 102.

According to this configuration, and upon the button 102 being inwardly depressed in the direction of arrow 110, a clearance is established between the internally configured slot 104 and the stem 106. At this point, a pulling or withdrawing force exerted by the coil spring 108 on the elongated stem 106, see arrow 112, with an opposite forward end 114 of the stem 106 being retracted from an engaging location with a downwardly angled abutment location of the tab 98.

It is noted that the spring 108 in the position of FIG. 10 is tensioned such that its bias is to pull the stem 106 along the direction of arrow 112. Releasing of the tab 98 from the forward edge abutment 114 of the stem 106 results in the coil spring 92 exerting a downward pivoting force causing the washer 84 to rotate about the hub 86 with the scoop 82 being caused to pivot upwardly as shown in FIG. 10. The construction of the button 102 is further such that it can be reset in order to reverse engage the stem 114 (in a direction opposite to arrow 112) to the tab 98.

Having described my invention, other and additional preferred embodiments will become apparent to those skilled in the art to which it pertains, and without deviating from the scope of the appended claims.

We claim:

1. A rongeur type bone removal device, comprising:
a pistol shaped body exhibiting a forward extending barrel, within which is configured an interior communicating surface and from which projects a powered belt, a plurality of linearly spaced apart blades being supported upon said belt, each of said blades exhibiting outer incising edges extending at an angle relative an axis extending through said barrel;
a passageway extending through an interior of the barrel and including a forward end communicating with a rear of said belt, said passageway including a rearward end in communication with an open cavity at an upper location of said body;
a debris collection chamber including an enclosed structure with a nipple protruding from an end face of the enclosed structure, said collection chamber being configured to be inserted into said open cavity of said body wherein when said collection chamber is inserted into said body, said nipple is in fluid communication with said rearward end of said passageway and said collection chamber is mounted within said body in proximity to a handle of said body; and
a power supply incorporated into the body and configured to, upon the actuation of a trigger, to close a circuit in order for the device to successively excise increments of bone for evacuation through said passageway and into said collection chamber.

2. The device as described in claim 1, further comprising said powered belt and supported blades incorporated into an attachment which is removably engageable to said forward barrel end.

3. The device as described in claim 1, said interior communicating surface further comprising a longitudinally exposed upper surface extending to an end location of said barrel.

4. The device as described in claim 3, said drive component further comprising forward and rearward spaced drive pins.

5. The device as described in claim 1, said interior communicating surface further comprising an arcuately recessed forward edge of said barrel, said drive component further including a rotary driven wheel mounted proximate said forward edge.

6. The device as described in claim 1, further comprising a lens incorporated into a forward location of said barrel and, in combination with an illuminating light source, providing imaging of a bone removal operation.

7. The device as described in claim 6, further comprising a video display integrated into said body above said handle and receiving an image generated by said lens.

* * * * *